(12) United States Patent
Leuthardt et al.

(10) Patent No.: US 9,259,248 B2
(45) Date of Patent: *Feb. 16, 2016

(54) ELECTRODE FOR STIMULATING BONE GROWTH, TISSUE HEALING AND/OR PAIN CONTROL, AND METHOD OF USE

(71) Applicant: Washington University, St. Louis, MO (US)

(72) Inventors: Eric C. Leuthardt, St. Louis, MO (US); Daniel W. Moran, Ballwin, MO (US)

(73) Assignee: WASHINGTON UNIVERSITY, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/308,063

(22) Filed: Jun. 18, 2014

(65) Prior Publication Data

US 2014/0336704 A1 Nov. 13, 2014

Related U.S. Application Data

(63) Continuation of application No. 12/089,104, filed as application No. PCT/US2006/038699 on Oct. 3, 2006, now Pat. No. 8,784,411.

(60) Provisional application No. 60/813,633, filed on Oct. 3, 2005.

(51) Int. Cl.
*A61B 18/18* (2006.01)
*A61B 17/70* (2006.01)
(Continued)

(52) U.S. Cl.
CPC ............. *A61B 17/7061* (2013.01); *A61B 17/80* (2013.01); *A61B 17/8625* (2013.01);
(Continued)

(58) Field of Classification Search
CPC ............... A61N 1/0551; A61N 1/0558; A61B 2018/1405
USPC .................................................. 606/27, 32, 41
See application file for complete search history.

(56) References Cited

U.S. PATENT DOCUMENTS 3,918,440 A * 11/1975 Kraus ............................... 602/2
4,318,792 A * 3/1982 Snow ............................. 205/118
(Continued)

FOREIGN PATENT DOCUMENTS

GB 2289416 A 11/1995
JP 2005021420 A 1/2005

OTHER PUBLICATIONS

Extended European Search Report for Application No. 06816154.6, Nov. 4, 2009, 9 pages.

*Primary Examiner* — William Thomson
*Assistant Examiner* — John R Downey
(74) *Attorney, Agent, or Firm* — Armstrong Teasdale LLP

(57) ABSTRACT

A system for use in stimulating at least one of bone growth, tissue healing and pain control in a patient includes a first screw and a second screw. The first screw has an elongate shaft with opposite ends and a length extending between the ends, an exterior surface and a screw thread formed on the exterior surface of the shaft and extending along at least a portion of the length. The screw thread has an electrically conducting portion and an electrically insulating portion. The electrically conducting portion is located for deposition in a first pre-specified portion of the patient and the electrically insulating portion is located for deposition in a second pre-specified portion of the patient. An electrical power source is adapted to pass electrical current through the patient between the first and second screws. The electrical power source is operatively connected to the first screw for conveying current through the electrically conducting portion of the screw thread to the first pre-specified portion. The electrically insulating portion inhibits current from being conveyed to the second pre-specified portion.

19 Claims, 5 Drawing Sheets

(51) Int. Cl.
*A61N 1/20* (2006.01)
*A61B 17/80* (2006.01)
*A61B 17/86* (2006.01)
*A61N 1/05* (2006.01)
*A61N 1/32* (2006.01)

(52) U.S. Cl.
CPC .............. *A61N1/0558* (2013.01); *A61N 1/205* (2013.01); *A61B 17/7037* (2013.01); *A61B 17/7059* (2013.01); *A61N 1/326* (2013.01)

(56) References Cited

U.S. PATENT DOCUMENTS

| | | | |
|---|---|---|---|
| 4,333,469 A | 6/1982 | Jeffcoat et al. | |
| 4,548,208 A | 10/1985 | Niemi | |
| 4,549,546 A | 10/1985 | Kelly et al. | |
| 4,549,547 A | 10/1985 | Brighton et al. | |
| 4,590,946 A * | 5/1986 | Loeb | 600/375 |
| 4,854,865 A | 8/1989 | Beard et al. | |
| 4,889,111 A | 12/1989 | Ben-Dov | |
| 5,030,236 A | 7/1991 | Dean | |
| 5,196,015 A * | 3/1993 | Neubardt | 600/554 |
| 5,383,784 A * | 1/1995 | Sernetz | 433/7 |
| 5,455,432 A * | 10/1995 | Hartsell et al. | 257/77 |
| 5,531,787 A | 7/1996 | Lesinski et al. | |
| 5,743,844 A | 4/1998 | Tepper et al. | |
| 6,034,295 A | 3/2000 | Rehberg et al. | |
| 6,112,122 A | 8/2000 | Schwardt et al. | |
| 6,120,502 A * | 9/2000 | Michelson | 606/247 |
| 6,605,089 B1 | 8/2003 | Michelson | |
| 6,678,562 B1 | 1/2004 | Tepper et al. | |
| 6,778,861 B1 * | 8/2004 | Liebrecht et al. | 607/116 |
| 6,918,907 B2 * | 7/2005 | Kelly et al. | 606/41 |
| 7,736,334 B2 * | 6/2010 | Mehier | 604/113 |
| 2002/0016616 A1 | 2/2002 | McGraw et al. | |
| 2004/0102828 A1 * | 5/2004 | Lowry et al. | 607/116 |
| 2004/0181216 A1 | 9/2004 | Kelly et al. | |
| 2004/0243207 A1 * | 12/2004 | Olson et al. | 607/116 |
| 2005/0059972 A1 | 3/2005 | Biscup | |
| 2010/0106198 A1 * | 4/2010 | Adcox et al. | 606/301 |

* cited by examiner

ELECTRODE FOR STIMULATING BONE GROWTH, TISSUE HEALING AND/OR PAIN CONTROL, AND METHOD OF USE

CROSS-REFERENCE TO RELATED APPLICATIONS

This application is a continuation application claiming priority from U.S. patent application Ser. No. 12/089,104 filed on Aug. 30, 2008, which claims priority from U.S. Provisional Patent Application Ser. No. 60/813,633 filed on Oct. 3, 2005 and PCT Patent Application No. PCT/US2006/038699 filed on Oct. 3, 2006. Each of these applications is incorporated herein by reference in their entirety.

FIELD

The present invention relates generally to stimulating bone growth and tissue healing, and more particularly to a method and apparatus for stimulating bone growth and tissue healing by applying an electrical current to the bone and adjacent soft tissue through a partially insulated screw.

BACKGROUND

Bone growth is desirable in many instances, such as when vertebrae in a patient's spine are fused to overcome pain and other effects caused by inter-vertebral movement or intra-vertebral movement. Although bone growth occurs naturally, it can be stunted or stopped by various factors such as tobacco, alcohol and steroid usage, poor bone stock, and age. Moreover, stimulating bone growth to speed recovery is desirable in some instances such as when an injured athlete wishes to return to her sport quickly. Thus, there is a need for stimulating bone growth in individuals.

Bone growth can be stimulated by various means. One such means for stimulating bone growth is by passing an electrical current through the bone. When fusing vertebrae in a patient's spine, various means have been used to stimulate bone growth. For example, some stimulators include wire electrodes embedded in bone fragments grafted to a region of the patient's back containing the vertebrae to be fused. Direct electrical current is applied to the electrodes to stimulate bone growth and fuse the fragments and adjoining vertebrae. To permit the current to be applied for extended periods of time while permitting the patient to be mobile, a generator is connected to the wire electrodes and implanted between the skin and muscle near the patient's vertebral column. The generator provides a continuous low amperage direct current (e.g., 20 µA) for an extended period of time (e.g., six months). After the vertebrae are fused, the generator and leads are surgically removed. Although these embedded electrodes are generally effective, the wire electrodes are susceptible to failure, requiring additional surgery to repair them. Moreover, placement of the wire electrodes is less than precise, allowing some of the current to pass through areas of tissue and bone where it is unneeded and where the current could potentially have adverse effects. Further, imprecise placement may require more energy to be provided to the electrodes than otherwise necessary to be optimally effective. Thus, there are several drawbacks and potential problems associated with devices such as these.

Although small amounts of bone movement can stimulate growth, it is generally desirable to limit movement between the bones or bone fragments being fused. There are several known means for limiting bone movement. Among these means for limiting bone movement are plates, rods and screws.

The plates and rods are typically held in position by screws which are mounted in the bone or bones being fused. FIG. 1 illustrates screws (generally designated by 10) driven into a vertebra 12 to immobilize the vertebra. As previously mentioned, the screws 10 are used for attaching rods 14 and/or plates (not shown) to vertebrae to hold the vertebrae in position while they fuse. Although these screws work well for their intended purpose, they do not facilitate electrically stimulating the region. Moreover, if electrical stimulation were applied to bones having conventional screws, the screws could potentially conduct current to areas of tissue and bone where the current is unneeded and where the current could potentially have adverse effects. Thus, there are drawbacks and potential problems associated with conventional screws such as these.

Beyond the well defined role of electrical fields within bone formation, electrical fields have also shown significant promise in aiding healing and recovery in nerve and spinal cord injury. Stimulating tissue healing with electrical currents has been demonstrated to be efficacious in animal models and is now being attempted experimentally in human subjects. Further, spinal cord and nerve root injury has been known to cause associated debilitating pain syndromes which are resist treatment. These pain syndromes also have shown improvement with pulsed electrical stimulation. Given these findings it is envisioned that apparatus providing a specified and confined electrical field through bony constructs and adjacent tissue (e.g., neural tissue) will facilitate an enhanced recovery from spinal cord and nerve injury, including improved functional outcome, better wound healing, and a higher level of pain control.

SUMMARY

In one aspect, a system for use in stimulating at least one of bone growth, tissue healing and pain control in a patient generally comprises a first screw and a second screw. The first screw has an elongate shaft with opposite ends and a length extending between the ends, an exterior surface and a screw thread formed on the exterior surface of the shaft and extending along at least a portion of the length. The screw thread has an electrically conducting portion and an electrically insulating portion. The electrically conducting portion is located for deposition in a first pre-specified portion of the patient and the electrically insulating portion is located for deposition in a second pre-specified portion of the patient. An electrical power source is adapted to pass electrical current through the patient between the first and second screws. The electrical power source is operatively connected to the first screw for conveying current through the electrically conducting portion of the screw thread to the first pre-specified portion. The electrically insulating portion inhibits current from being conveyed to the second pre-specified portion.

In another aspect, a system for use in stimulating at least one of bone growth, tissue healing and pain control in a patient generally comprises a first screw having an elongate shaft with opposite ends and a length extending between the ends, an exterior surface and a screw thread formed on the exterior surface of the shaft and extending along at least a portion of the length. The screw thread has an electrically conducting portion and an electrically insulating portion. The electrically conducting portion is located for deposition in a first pre-specified portion of the bone and bone related tissue and the electrically insulating portion is located for deposition in a second pre-specified portion of the bone and bone related tissue. A second screw has an elongate shaft with opposite ends and a length extending between the ends, an exterior surface and a screw thread formed on the exterior surface of the shaft and extending along at least a portion of the length. The screw thread has an electrically conducting portion and an electrically insulating portion. The electrically conducting portion is located for deposition in the first pre-specified portion of the bone and bone related tissue and the electrically insulating portion is located for deposition in the second pre-specified portion of the bone and bone related tissue. An electrical power source is adapted to pass electrical current between the first and second screw.

In yet another aspect, a system for use in stimulating at least one of bone growth, tissue healing and pain control in a patient generally comprises a first screw and a second screw. The first screw has an elongate shaft with opposite ends and a length extending between the ends, an exterior surface and a screw thread formed on the exterior surface of the shaft and extending along at least a portion of the length. The screw thread has an electrically conducting portion and an electrically insulating portion. The electrically conducting portion is located for deposition in a first pre-specified portion of the patient and the electrically insulating portion is located for deposition in a second pre-specified portion of the patient. A plate has at least two openings sized and shaped for receiving the first and second screws. An electrical power source is adapted to pass electrical current between the first and second screw. The electrical power source is operatively connected to the first screw for conveying current through the electrically conducting portion of the screw thread to the first pre-specified portion. The electrically insulating portion inhibits current from being conveyed to the second pre-specified portion.

BRIEF DESCRIPTION OF THE DRAWINGS

Corresponding reference characters indicate corresponding parts throughout the several views of the drawings.

DETAILED DESCRIPTION AN EMBODIMENT

Figure 2:
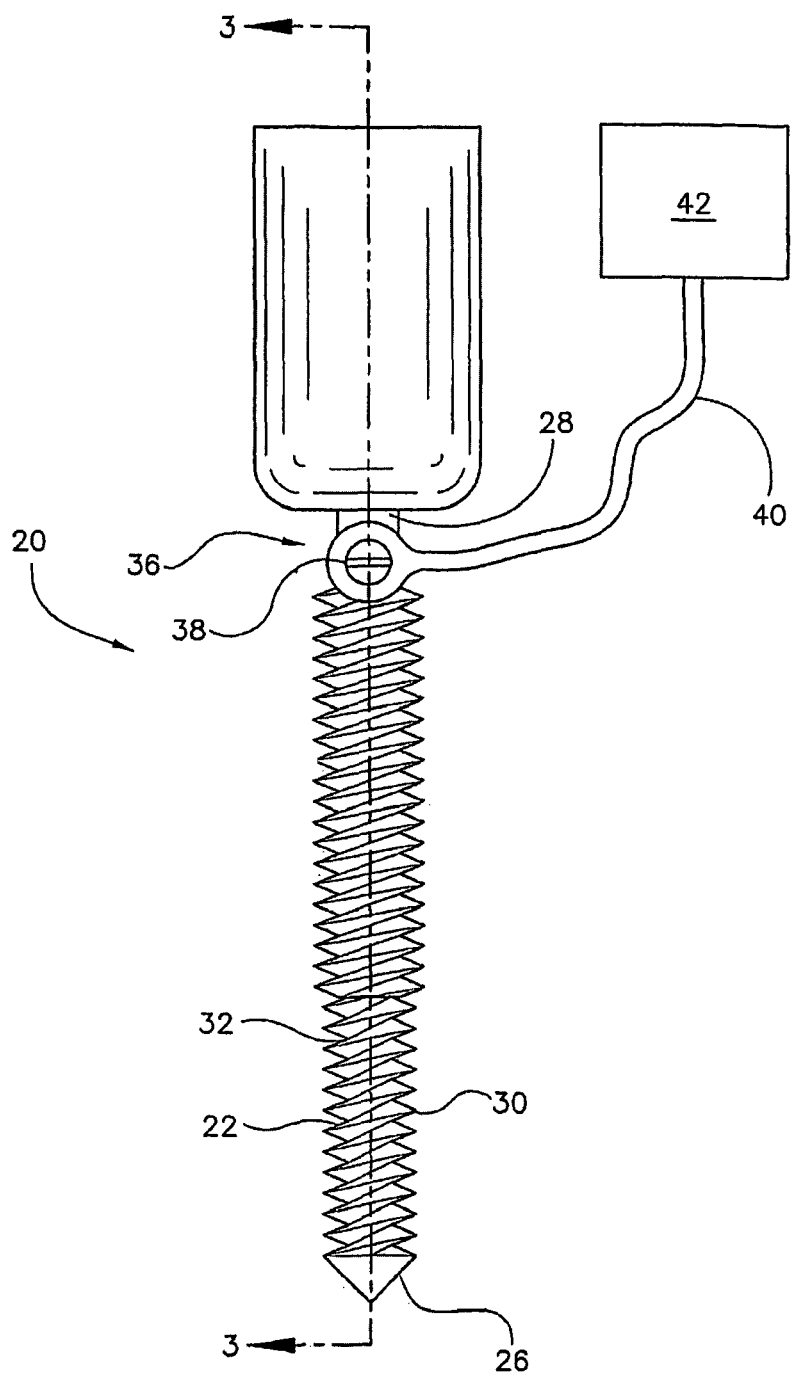
FIG. 2 is a side elevation of a screw of the present invention.

Referring now to the drawings and in particular to FIG. 2, a screw or electrode of the present invention is designated in its entirety by the reference numeral 20. The screw 20 has an elongate shaft 22 having a length 24 (FIG. 3) extending between opposite ends 26, 28. A conventional screw thread 30 is formed on an exterior surface 32 of the shaft 22. The thread 30 extends along at least a portion of the length 24 of the shaft 22. The screw 20 also includes a head 34 adjacent the one end 28 of the shaft 22. The head 34 is shaped for engaging the screw 20 with a driver or wrench to rotate the screw and thereby drive it into bone. In one embodiment, the head 34 includes a connector, generally designated by 36, adjacent its head 34 for connecting an electrical conductor to the screw 20 as will be explained in further detail below. In one embodiment, the connector 36 includes a screw fastener 38 threaded into the screw 20 for holding the electrical lead. As illustrated in FIG. 2, an electrical conductor 40 is electrically connectable to the screw 20 and to an electrical power source 42 for conveying electrical current through the shaft. In one embodiment the power source 42 produces direct current. In another embodiment, the power sources 42 produces alternating current such as a time-varying current waveform (e.g., a sine wave or a square wave) having a frequency between nearly zero hertz and ten gigahertz. Although other electrical conductors 40 may be used without departing from the scope of the present invention, in one embodiment the conductor is a 35 gauge insulated braided stainless steel wire. It is further envisioned that the connector 36 may take other forms. For example, the connector may be a threaded terminal and nut, a fastenerless connector, a quick disconnect type connector, a soldered pin, or an adhesive without departing from the scope of the present invention.

Figure 3:
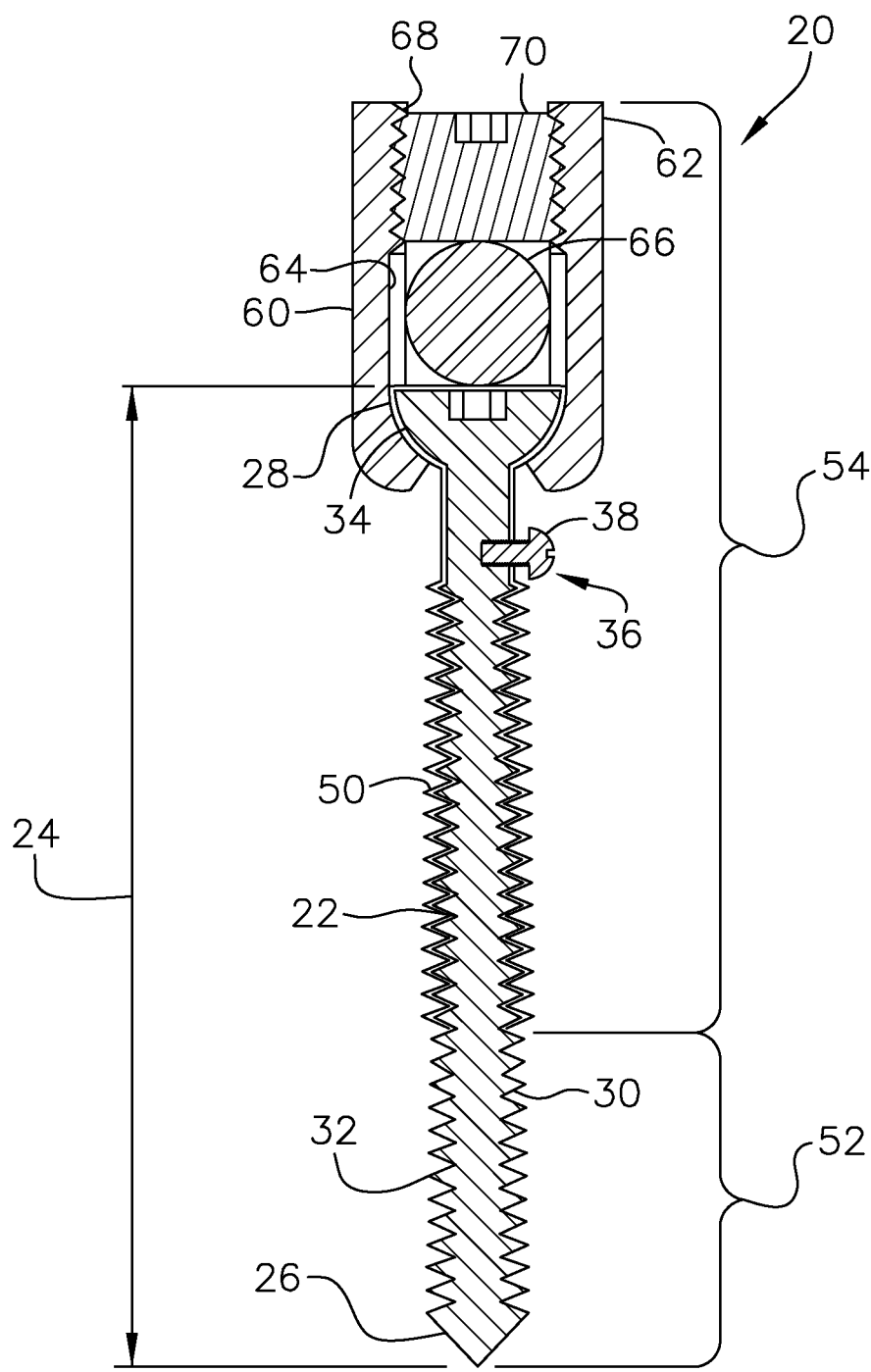
FIG. 3 is a cross section of the screw taken along line 3-3 of FIG. 2.

As illustrated in FIG. 3, the shaft 22 is generally conductive, but a portion of the shaft is coated with an insulating coating 50. Thus, the shaft 22 has an electrically conducting portion 52 and an electrically insulating portion 54. Although the conducting portion 52 of the screw 20 may have other lengths without departing from the scope of the present invention, in one embodiment the conducting portion of the screw has a length of less than about three centimeters. In one embodiment, the conducting portion 52 of the screw 20 has a length of between about three millimeters and about three centimeters. Further, although the conducting portion 52 of the screw 20 may be positioned at other locations along the screw, in one embodiment the conducting portion of the screw is positioned adjacent the end 26 of the screw opposite the head 34. In another embodiment (not shown), the conducting portion 52 of the screw 20 is positioned between the ends 26, 28 of the screw, and each end of the screw is electrically insulated. Although the insulating portion 54 of the screw 20 may have other lengths without departing from the scope of the present invention, in one embodiment the insulating portion of the shaft extends at least forty percent of the length of the screw. In another embodiment, the insulating portion 54 of the shaft 22 extends between about fifty percent of the length of the screw 20 and about ninety five percent of the length of the screw.

In one embodiment, a clevis 60 is attached to the screw 20. The clevis 60 pivots freely on the head 34 of the screw and includes a pair of legs 62 defining an opening 64 adapted to receive a rod 66. The legs 62 include threads 68 for engaging a screw 70 for fastening the rod 66 in the opening 64 and preventing the clevis 60 from pivoting on the screw head 34. Other features of the screw 20 and clevis 60 are conventional and will not be described in further detail.

As will be appreciated by those skilled in the art, the screw 20 comprises an electrically conductive material such as a titanium alloy and the electrically insulating portion of the shaft is coated with an insulating material such as titanium dioxide. In one embodiment, the insulating material is formed by anodizing the exterior surface of a portion of the shaft. The conductivity of the screw 20 in the conducting portion 52 may be improved by coating the screw with a highly conductive material such as titanium nitride. Both treated surfaces, titanium dioxide and titanium nitride, are extremely adherent to the titanium and therefore not likely to be breached when screwed into bone. Because methods for anodizing and/or coating titanium parts are well known by those having ordinary skill in the art, they will not be described in further detail.

Figure 1:
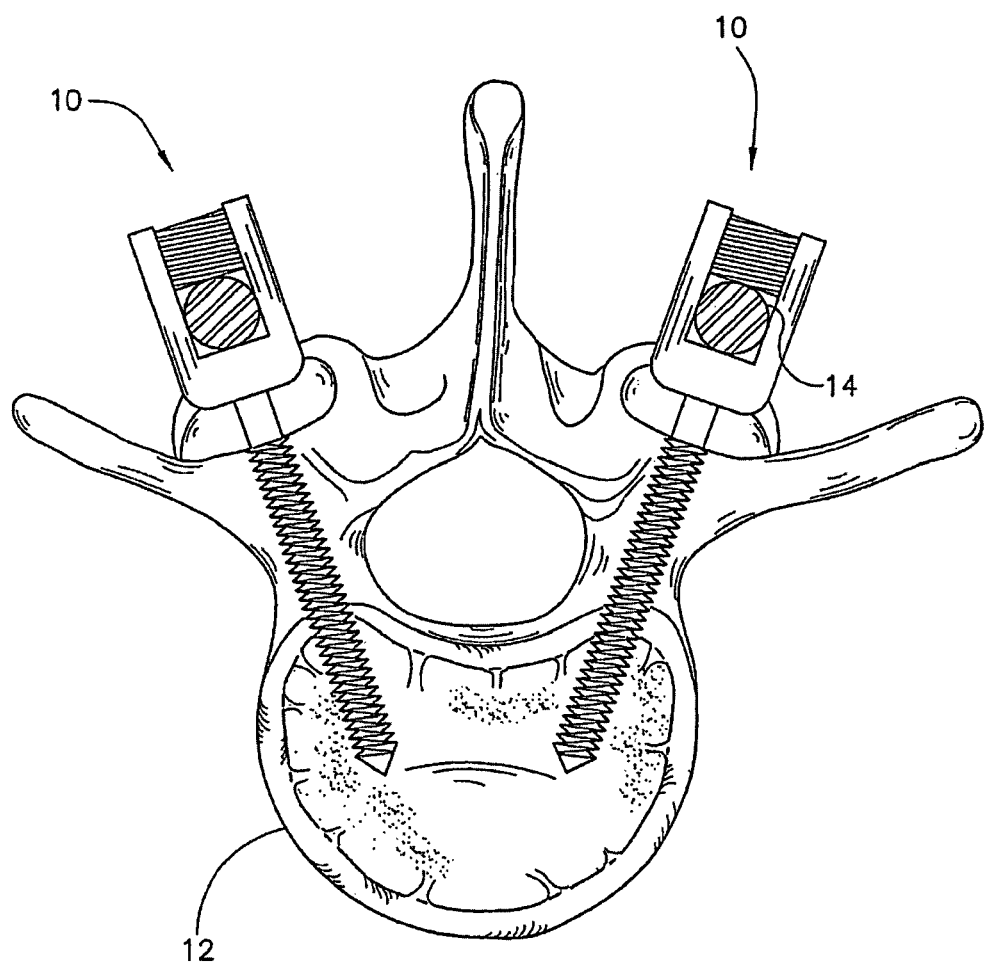
FIG. 1 is a horizontal cross section of a conventional electrically conductive screw installed in a vertebra.

The screws 20 are used in pairs so an electrical circuit is completed from the bone into which the screws are driven. As will be appreciated by those skilled in the art, the current travels through the conductive portion of the screw 20 from the conductor 40 to the bone in which the screw 20 is inserted (e.g., a vertebra such as vertebra 12 in FIG. 1) as will be explained in more detail below. The current does not pass through the coating on the insulated portion 54 of the shaft 22 so that the current may be directed to the portion of the bone where stimulation is most needed. As will be also appreciated, the insulated portion 54 of the shaft 22 prevents current from passing through portions of the bone and tissue where electrical current is not desired. The screw 20 of the present invention may be installed in the bone using conventional techniques. In most instances, the bone is pre-drilled to avoid splitting when the screw 20 is installed. It is envisioned in some instances the bone may be reinforced, such as with bands before the screw 20 is installed to provide support to the bone and prevent damage to it as the screw is installed.

Figure 4:
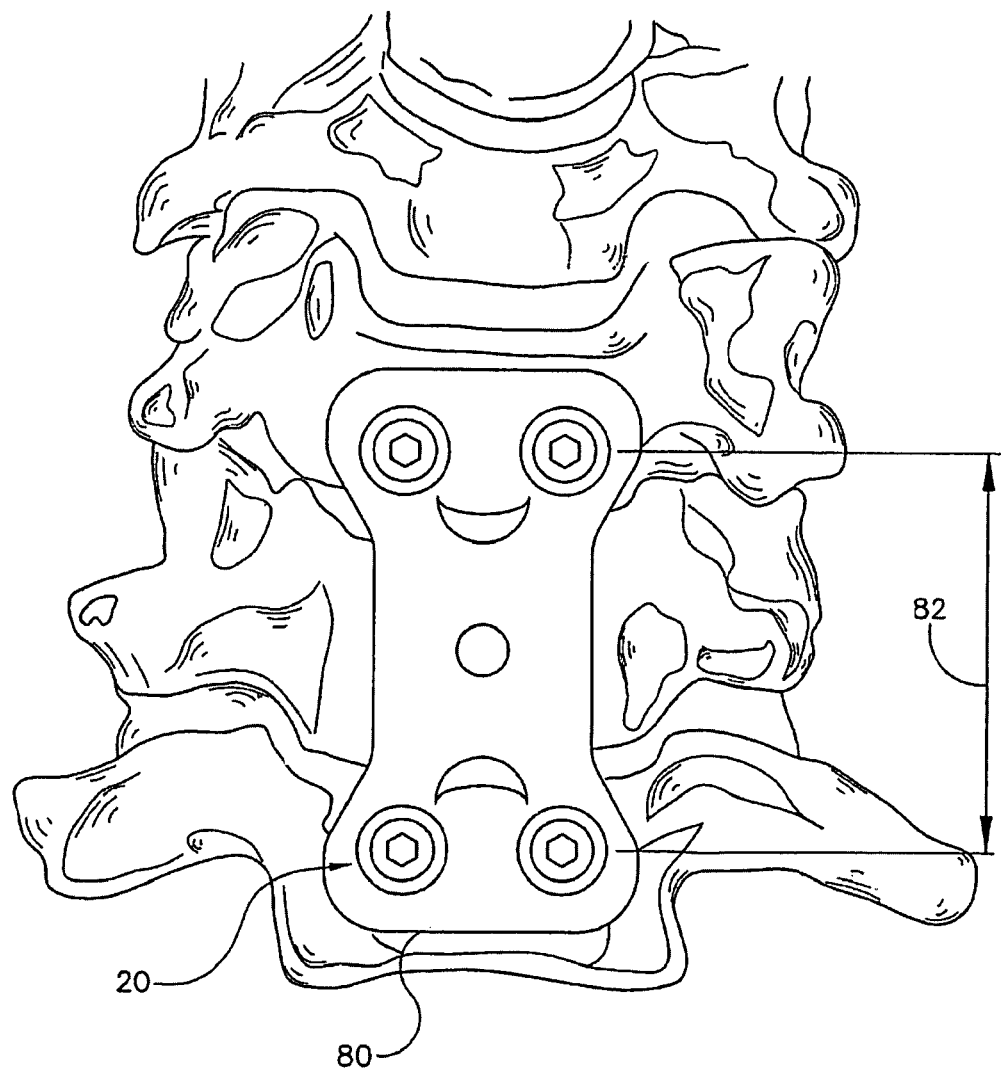
FIG. 4 is an front elevation of a portion of a spine with a first apparatus of the present invention installed thereon.
Figure 5:
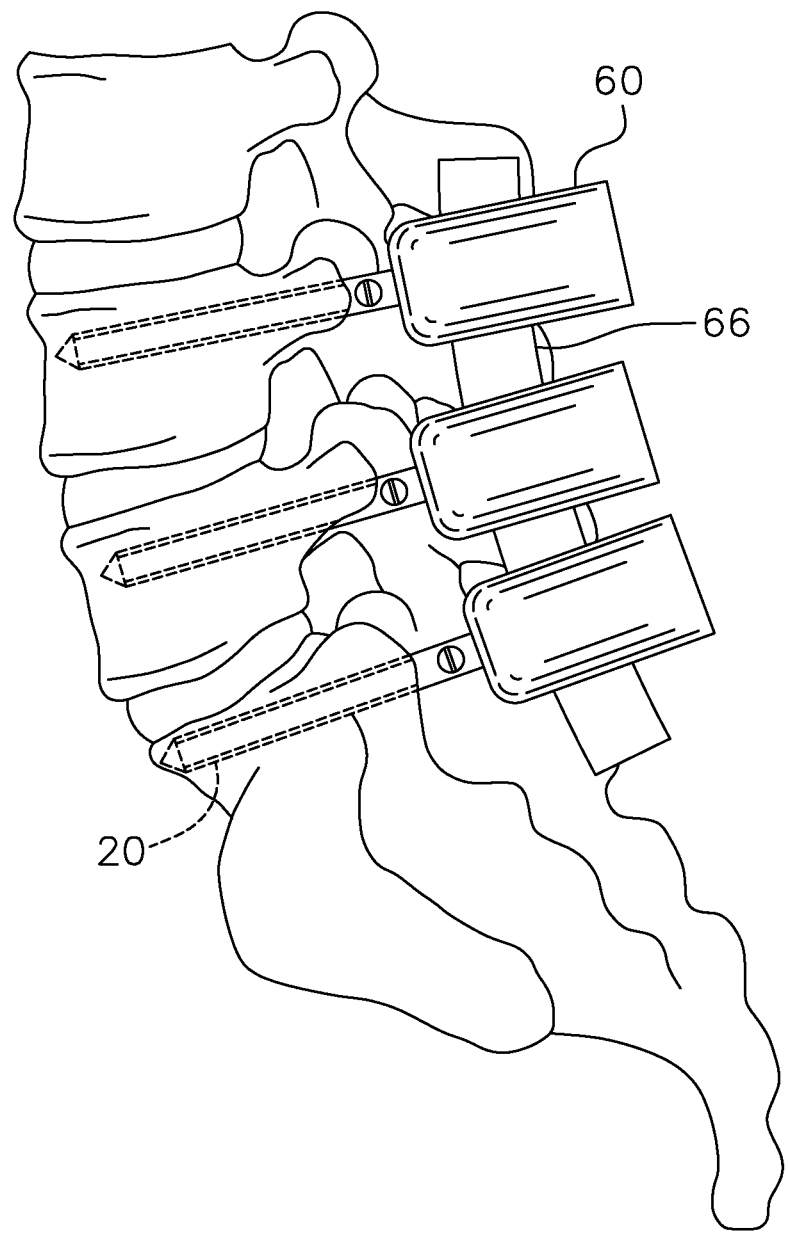
FIG. 5 is a side elevation of a portion of a spine with a second apparatus of the present invention installed thereon.

In some instances, it is envisioned that the screws 20 of the present invention may be used in combination with other appliances such as spacers. For example, in some applications the screws 20 may be installed through a plate 80 as shown in FIG. 4 to provide support for the bone and to guide proper spacing and positioning of the screws. The plate 80 has at least two openings (not shown) for receiving screws 20. Preferably, each of the openings are sized and shaped for receiving at least one screw 20. Although the openings in the plate 60 may have other spacings without departing from the scope of the present invention, in one embodiment the openings are spaced by a distance 82 of between about one centimeter and about two centimeters. In the embodiment shown in FIG. 5, the spacers are formed as rods 66 bridging the screws 20 as described above. As the configurations shown in FIGS. 4 and 5 are well known to those having ordinary skill in the art, they will not be described in further detail.

To use the apparatus of the present invention to stimulate bone growth, the bone (e.g., vertebra 12) is pre-drilled. A first screw 20 is inserting in the bone and driven into place by turning the screw. A second screw 20 is inserted in the bone at a predetermined distance from the first screw. Next, electrical conductors 40 are attached to the screws 20 and to an electrical power source 42 (e.g., a generator, a battery or an inductance coil positioned in a pulsing magnetic field). The conductors 40 are energized by the power source 42 so an electrical current passes through the bone. Because the screws 20 are partially insulated, the electrical current passes between only a portion of the first screw and only a portion of the second screw directing the current to a particular area of the bone or tissue. Although other amounts of current may be used, in one embodiment a direct current of between about one microamp and about one milliamp is used. In another embodiment, a direct current of between about twenty microamps and about sixty microamps is used. In other embodiments, the current may be any time-varying current waveform (e.g., a sine wave or a square wave) having a frequency between nearly zero hertz and ten gigahertz.

In addition to stimulating bone growth, it is envisioned that the apparatus and method described above may be used to improve tissue growth and healing, including soft tissue and nerve tissue. Thus, the apparatus and method may be useful in healing spinal cord and nerve root injury. Further, the apparatus and method may be useful in treating pain syndromes.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A system for use in stimulating at least one of bone growth, tissue healing and pain control in a patient, the system comprising:
    a first screw having an elongate shaft with opposite ends and a length extending between the ends, an exterior surface and a screw thread formed on the exterior surface of the shaft and extending along at least a portion of the length, said screw thread having an electrically conducting portion and an electrically insulating portion, the electrically conducting portion being located for deposition in a first pre-specified portion of the patient and the electrically insulating portion being located for deposition in a second pre-specified portion of the patient;
    a second screw spaced from the first screw; and
    an electrical power source connected, via conductors, to the first and second screws and adapted to pass electrical current through the patient between the first and second screws, the electrical power source being operatively connected to the first screw for conveying current through the electrically conducting portion of the screw thread to the first pre-specified portion, the electrically insulating portion inhibiting current from being conveyed to the second pre-specified portion.

2. The system set forth in claim 1 wherein the electrical power source is adapted to pass direct current between the first and second screws.

3. The system set forth in claim 2 wherein the electrical power source is adapted to pass direct current between one microamp and one milliamp between the first and second screws.

4. The system set forth in claim 3 wherein the electrical power source is adapted to pass direct current between twenty microamps and sixty microamps between the first and second screws.

5. The system set forth in claim 1 wherein the electrically conducting portion of the first screw is located for deposition in bone of the patient.

6. The system set forth in claim 1 wherein the electrically conducting portion of the first screw is located for deposition in at least one of soft tissue and nerve tissue of the patient.

7. The system set forth in claim 1 further comprising a plate having at least two openings therein for receiving the first and second screws.

8. The system set forth in claim 7 wherein the openings in the plate are spaced by a distance of between one centimeter and ten centimeters.

9. A system for use in stimulating at least one of bone growth, tissue healing and pain control in a patient, the system comprising:
    a first screw having an elongate shaft with opposite ends and a length extending between the ends, an exterior surface and a screw thread formed on the exterior surface of the shaft and extending along at least a portion of the length, said screw thread having an electrically conducting portion and an electrically insulating portion, the electrically conducting portion being located for deposition in a first pre-specified portion of the bone and bone related tissue and the electrically insulating portion being located for deposition in a second pre-specified portion of the bone and bone related tissue;
    a second screw having an elongate shaft with opposite ends and a length extending between the ends, an exterior surface and a screw thread formed on the exterior surface of the shaft and extending along at least a portion of the length, said screw thread having an electrically conducting portion and an electrically insulating portion, the electrically conducting portion being located for deposition in the first pre-specified portion of the bone and bone related tissue and the electrically insulating portion being located for deposition in the second pre-specified portion of the bone and bone related tissue; and an electrical power source connected, via conductors, to the first and second screws for passing electrical current between the first and second screw.

10. The system set forth in claim 9 wherein the electrical power source is adapted to pass direct current between the first and second screws.

11. The system set forth in claim 10 wherein the electrical power source is adapted to pass direct current between one microamp and one milliamp between the first and second screws.

12. The system set forth in claim 11 wherein the electrical power source is adapted to pass direct current between twenty microamps and sixty microamps between the first and second screws.

13. The system set forth in claim 9 wherein the electrical power source is adapted to pulse electrical current between the first and second screws.

14. The system set forth in claim 9 wherein the electrical power source is adapted to direct a current having a frequency less than 10 gigahertz between the first and second screws.

15. A system for use in stimulating at least one of bone growth, tissue healing and pain control in a patient, the system comprising:

a first screw having an elongate shaft with opposite ends and a length extending between the ends, an exterior surface and a screw thread formed on the exterior surface of the shaft and extending along at least a portion of the length, said screw thread having an electrically conducting portion and an electrically insulating portion, the electrically conducting portion being located for deposition in a first pre-specified portion of the patient and the electrically insulating portion being located for deposition in a second pre-specified portion of the patient, a second screw spaced from the first screw;

a plate having at least two openings sized and shaped for receiving the first and second screws; and an electrical power source connected, via conductors, to the first and second screws for passing electrical current between the first and second screw, the electrical power source being operatively connected to the first screw for conveying current through the electrically conducting portion of the screw thread to the first pre-specified portion, the electrically insulating portion inhibiting current from being conveyed to the second pre-specified portion.

16. The system set forth in claim 15 wherein the openings in the plate are spaced by a distance between one centimeter and ten centimeters.

17. The system set forth in claim 16 wherein the openings in the plate are spaced by a distance between one centimeter and two centimeters.

18. The system set forth in claim 15 further comprising a rod bridging the first and second screws.

19. The system set forth in claim 15 wherein the electrically conducting portion is located for deposition in a vertebra of the patient.

* * * * *